(12) United States Patent
Kelly et al.

(10) Patent No.: US 6,365,615 B1
(45) Date of Patent: Apr. 2, 2002

(54) SMALL MOLECULES USEFUL IN THE TREATMENT OF INFLAMMATORY DISEASE

(75) Inventors: Terence Alfred Kelly, Ridgefield; Jiang-Ping Wu; Daniel Kuzmich, both of Danbury, all of CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/605,675

(22) Filed: Jun. 28, 2000

Related U.S. Application Data

(60) Provisional application No. 60/144,894, filed on Jul. 21, 1999.

(51) Int. Cl.[7] ............... A61K 31/415; C07D 235/00; C07D 213/00
(52) U.S. Cl. ............ 514/386; 514/397; 514/400; 546/1; 548/300.1; 548/302.7; 548/317.1; 548/453; 548/517; 548/545
(58) Field of Search ............... 514/386, 397, 514/400; 548/300.1, 302.7, 317.1, 453, 517, 545; 546/1

(56) References Cited

U.S. PATENT DOCUMENTS

| | | | |
|---|---|---|---|
| 3,668,217 A | 6/1972 | Fujinami et al. ......... 260/369.5 |
| 3,741,981 A | 6/1973 | Fujinami et al. ......... 260/326.5 |
| 3,846,441 A | 11/1974 | Mine et al. ............. 286/369.3 |
| 4,911,748 A | 3/1990 | Prisbylla .................... 548/313 |
| 4,944,791 A | 7/1990 | Schroeder et al. ............ 71/92 |
| 4,977,270 A | 12/1990 | Wee .......................... 548/314 |
| 5,208,250 A | 5/1993 | Cetenko et al. ............ 514/369 |
| 5,306,822 A | 4/1994 | Cetenko et al. ............ 548/226 |
| 5,334,606 A | 8/1994 | MacLeod ................... 514/376 |
| 5,464,856 A | 11/1995 | Cetenko et al. ............ 514/369 |
| 5,750,553 A | 5/1998 | Claussner et al. .......... 514/392 |

FOREIGN PATENT DOCUMENTS

| | | |
|---|---|---|
| DE | 19 40 032 A1 | 3/1970 |
| DE | 19 58 183 A1 | 6/1970 |
| DE | 21 00 800 A1 | 7/1971 |
| EP | 0 091 596 A1 | 10/1983 |
| EP | 0 343 643 A1 | 11/1989 |
| EP | 0 545 478 A1 | 6/1993 |
| JP | 51-88631 | 8/1976 |
| WO | WO 95 18794 A1 | 7/1995 |
| WO | 9808813 * | 3/1998 |
| WO | WO 98 39303 A1 | 9/1998 |
| WO | WO 99 11258 A1 | 3/1999 |
| WO | WO 99 49856 A2 | 10/1999 |

OTHER PUBLICATIONS

Issartel et al. in"Eur.J.Med.Chem.",New 7–OH–1,3–diazbicyclo octane der.:evaln . . . immunomodulating. . ;31/9/ 717–23(1996).*

Takayama, et al; "Quantitative Structure–activity Relationships of Antifungal 1–(3,5– Dichlorophenyl)–2,5–pyrrolidinediones and 3–(3,5–Diochlorophenyl) –2,4–oxazolidinediones"; Agric. Biol. Chem. 1982, 46, 2755–8.

Li, et al; "Examination of the Interrelationship Between Aliphatic Group Dipole moment and Polar Substituent Constants" J. Pharm. Sci. 1984; 73, 553–8.

Halim, et al; "3–[2–(3,5–Dimethylpyrazolyl)] Succinic Anhydride: Synthone for the Synthesis of Some Heterocycles with Potential Pharmaceutical Activity"; Monatshefte fuer Chemie, 1994, 125 1437–1442.

Database CA on STN, Chemical Abstracts, (Columbus, OH, USA) No. 128:204801, Hollinshead,S. et al, "Combinatorial process for preparing substituted pyrrolidine libraries", Abstract WO 98 08813, Mar. 1998.

Database CA on STN, Chemical Abstracts, (Columbus, OH, USA) No. 124:145896, Drewes, M. et al, "Preparation of 4–(heterocyclo)–2–(sulfonamido) benzonitrile selective herbicides", abstract DE4414568, Nov. 1995.

(List continued on next page.)

Primary Examiner—Richard L. Raymond
Assistant Examiner—Sudhaker B. Patel
(74) Attorney, Agent, or Firm—Robert P. Raymond; Alan R. Stempel; Mary-Ellen M. Devlin

(57) ABSTRACT

Novel compounds of the formula I

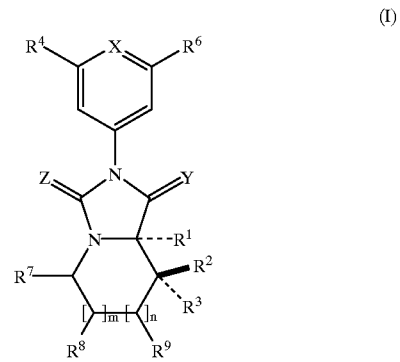

which are useful for treating or preventing inflammatory and immune cell-mediated diseases. Exemplary compounds are:

2-(3,5-Dichlorophenyl)-7-(R*)-phenyl-7a-(R*)-tetrahydropyrrolo[1,2-c]imidazole-1,3-dione;

2-(3,5-Dichlorophenyl)-7a-(R*)-methyl-7-(R*)-phenyl-tetrahydropyrrolo[1,2-c]imidazole-1,3-dione; and, 7-(R*)-(4-Bromophenyl)-2-(3,5-dichlorophenyl)-7a-(R*)-tetrahydropyrrolo[1,2-c]imidazole-1,3-dione.

4 Claims, No Drawings

OTHER PUBLICATIONS

Musza, L. L., et al, "Potent New Call Adhesion Inhibitory Compounds from the Root of *Trichilia rubra*"; Tetrahedron, 1994, 50, 11369–11378.

Boschelli, D. H., et al; "3–Alkoxybenzo[b]thiophene–2–carboxamides as Inhibitors of Neutrophil–Endothelial Cell Adhesion"; J. Med. Chem, 1994., 37, 717.

Boschelli, D. H., et al; "Inhibition of E–Selectin–, ICAM–1–, and VCAM–1–Mediated Cell Adhesion by Benzo[b]thiophene–, Benzofuran–, Indole–, and Naphthalene–2–carboxamides: Identification of PD 144795 as an Antiinflammatory Agent"; J. Med. Chem., 1995, 38, 4597–4614.

Sanfilippo, P. J., et al; "Novel Thiazole Based Heterocycles as Inhibitors of LFA–1/ICAM–1 Mediated Cell Adhesion"; J. Med. Chem. 1995, 38, 1057–1059.

* cited by examiner

SMALL MOLECULES USEFUL IN THE TREATMENT OF INFLAMMATORY DISEASE

RELATED APPLICATIONS

The benefit of prior provisional application serial number 60/144,894, filed on Jul. 21, 1999, is hereby claimed.

FIELD OF THE INVENTION

The present invention relates generally to a series of novel small molecules, their synthesis and their use in the treatment of inflammatory disease.

BACKGROUND OF THE INVENTION

Research spanning the last decade has helped to elucidate the molecular events attending cell-cell interactions in the body, especially those events involved in the movement and activation of cells in the immune system. See generally, Springer, T. *Nature*, 1990, 346, 425–434. Cell surface proteins, and especially the Cellular Adhesion Molecules ("CAMs") and "Leukointegrins" including LFA-1, MAC-1 and gp 150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117–138 and Diamond, M.; Springer, T. *Current Biology*, 1994, 4, 506–532.

A group of individuals has been identified which lack the appropriate expression of Leukointegrins, a condition termed "Leukocyte Adhesion Deficiency" (Anderson, D. C.; et al., *Fed. Proc.* 1985, 44, 2671–2677 and Anderson, D. C.; et al., *J. Infect. Dis.* 1985, 152, 668–689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component, Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today*, 1994, 15, 251–255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*; Wegner, C. D., Ed.; 1994, 1–38, Cosimi, C. B.; et al., *J. Immunol.* 1990, 144, 4604–4612 and Kavanaugh, A.; et al., *Arthritis Rheum.* 1994, 37, 992–1004) and antibodies directed against LFA-1 have demonstrated immunosuppressive effects in bone marrow transplantation and in the prevention of early rejection of renal allografts (Fischer, A.; et al., *Lancet*, 1989, 2, 1058–1060 and Le Mauff, B.; et al., *Transplantation*, 1991, 52, 291–295).

It has also been demonstrated that a recombinant soluble form of ICAM-1 can act as an inhibitor of the ICAM-1 interaction with LFA-1. Soluble ICAM-1 acts as a direct antagonist of CD18, CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., *J. Immunol.* 1993, 151, 7224 and Roep, B. O.; et al., *Lancet*, 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-baged therapeutics are generally expensive to produce.

Several small molecules have been described in the literature which affect the interaction of CAMs and Leukointegrins. A natural product isolated from the root of Trichilia rubra was found to be inhibitory in an in vitro cell binding assay (Musza, L. L.; et al., *Tetrahedron*, 1994, 50, 11369–11378). One series of molecules (Boschelli, D. H.; et al., *J. Med. Chem.* 1994, 37, 717 and Boschelli, D. H.; et al., *J. Med. Chem.* 1995, 38, 4597–4614) was found to be orally active in a reverse passive Arthus reaction, an induced model of inflammation that is characterized by neutrophil accumulation (Chang, Y. H.; et al., *Eur. J. Pharmacol.* 1992, 69, 155–164). Another series of molecules was also found to be orally active in a delayed type hypersensitivity reaction in rats (Sanfilippo, P. J.; et al., *J. Med. Chem.* 1995, 38, 1057–1059). All of these molecules appear to act nonspecifically, either by inhibiting the transcription of ICAM-1 along with other proteins or act intracellularly to inhibit the activation of the Leukointegrins by an unknown mechanism. None of the molecules directly antagonize the interaction of the CAMs with the Leukointegrins. Due to lack of potency, lack of selectivity and lack of a specific mechanism of action, the described small molecules are not likely to be satisfactory for therapeutic use.

It follows that small molecules having the similar ability as large protein molecules to directly and selectively antagonize the binding of the CAMs to the Leukointegrins would make preferable therapeutic agents. WO9839303 discloses a class of small molecule inhibitors of the interaction of LFA-1 and ICAM-1. WO9911258 discloses that the fungal metabolite mevinolin and derivatives bind to LFA-1 and disrupt the interaction of LFA-1 and ICAM-1.

SUMMARY OF THE INVENTION

A first aspect of the invention comprises a method for treating or preventing inflammatory and immune cell-mediated diseases by the administration of certain novel small molecules. These compounds act by inhibiting the interaction of cellular adhesion molecules, specifically by antagonizing the binding of human intercellular adhesion molecules (including ICAM-1, ICAM-2 and ICAM-3) to the Leukointegrins (especially CD18/CD11a). A second aspect of the invention comprises novel small molecules having the above-noted therapeutic activities. A third aspect of the invention comprises methods for making these novel compounds. A final aspect of the invention comprises pharmaceutical compositions comprising the above-mentioned compounds suitable for the prevention or treatment of inflammatory and immune cell-mediated conditions.

DETAILED DESCRIPTION OF THE INVENTION

The invention comprises compounds of the formula I

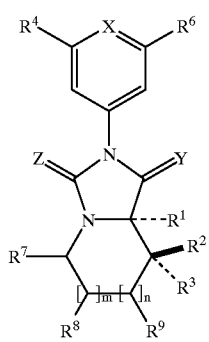

(I)

wherein:
is 0 or 1,
is 0 or 1, and
m+n is equal to either 1 or 2;
Y is an oxygen or sulfur atom;
Z is an oxygen or sulfur atom;
$R^1$ is:

(A) a hydrogen atom, or
(B) branched or unbranched alkyl of 1 to 3 carbon atoms or cycloalkyl of 3 to 5 carbon atoms wherein said alkyl or cycloalkyl group may optionally be substituted with:
  (i) a group of the formula —$OR^{10}$, wherein $R^{10}$ is an alkyl or acyl group of 1 to 2 carbon atoms,
  (ii) a group of the formula —$NR^{11}R^{12}$, wherein $R^{11}$ and $R^{12}$ are each, independently, alkyl of 1 to 2 carbon atoms, or acyl of 1 to 2 carbon atoms, or
(C) a group of the formula —$OR^{13}$, wherein $R^{13}$ is a an alkyl or acyl group of 1 to 2 carbon atoms;

$R^2$ is:
aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-midazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzor[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said aryl group may be optionally and independently replaced with:
  (i) $R^{14}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
  wherein one or more of the hydrogen atoms of said $R^{14}$ aryl group may be optionally and independently replaced with:
    (a) branched or unbranched alkyl of 1 to 6 carbon atoms or cycloalkyl of 3 to 6 carbon atoms, which alkyl or cycloakyl group may be mono- or polysubstituted with halogen or oxo,
    (b) a group of the formula —$COOR^{15}$, wherein $R^{15}$ is straight or branched alkyl of 1 to 5 carbon atoms or cycloalkyl of 3 to 5 carbon atoms,
    (c) a group of the formula —$NR^{16}R^{17}$, wherein $R^{16}$ and $R^{17}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{16}$ and $R^{17}$ constitute a saturated hydrocarbon bridge of 3 to 5 carbon atoms which together with the nitrogen atom between them form a heterocyclic ring, (d) a group of the formula —CONR$^{18}$R$^{19}$, wherein R$^{18}$ and R$^{19}$ are each independently a hydrogen atom, alkyl or fluoroalkyl of 1 to 6 carbon atoms or cycloalkyl of 3 to 6 carbon atoms, or wherein R$^{18}$ and R$^{19}$ constitute a saturated hydrocarbon bridge of 3 to 5 carbon atoms which together with the nitrogen atom between them form a heterocyclic ring, (e) a group of the formula —OR$^{20}$, wherein R$^{20}$ is a hydrogen atom, or an alkyl, fluoroalkyl or acyl group of 1 to 7 carbon atoms, (f) a group of the formula —SR$^{21}$, wherein R$^{21}$ is a hydrogen atom, or an alkyl, fluoroalkyl or acyl group of 1 to 7 carbon atoms, (g) cyano, (h) nitro, (i) halogen, (ii) methyl, which may be mono- or polysubstituted with fluorine atoms, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —COOR$^{22}$, wherein R$^{22}$ is straight or branched alkyl of 1 to 5 carbon atoms or cycloalkyl of 3 to 5 carbon atoms, (v) a group of the formula —NR$^{23}$R$^{24}$, wherein R$^{23}$ and R$^{24}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{23}$ and R$^{24}$ constitute a saturated hydrocarbon bridge of 3 to 5 carbon atoms which together with the nitrogen atom between them form a heterocyclic ring, (vi) a group of the formula —CONR$^{25}$R$^{26}$, wherein R$^{25}$ and R26 are each, independently, a hydrogen atom, alkyl or fluoroalkyl of 1 to 6 carbon atoms or cycloalkyl of 3 to 6 carbon atoms, or wherein R$^{25}$ and R$^{26}$ constitute a saturated hydrocarbon bridge of 3 to 5 carbon atoms which together with the nitrogen atom between them form a heterocyclic ring, (vii) a group of the formula —COR$^{27}$, wherein R$^{27}$ is a hydrogen atom, straight or branched alkyl of 1 to 5 carbon atoms, or cycloalkyl of 3 to 5 carbon atoms, (viii) a group of the formula —OR$^{28}$, wherein R$^{28}$ is a hydrogen atom, an alkyl, fluoroalkyl or acyl group of 1 to 7 carbon atoms, (ix) a group of the formula —SR$^{29}$, wherein R$^{29}$ is a hydrogen atom, an alkyl, fluoroalkyl or acyl group of 1 to 7 carbon atoms, (x) cyano, (xi) nitro, or (xii) halogen, R$^3$ is:

(A) a hydrogen atom, or (B) branched or unbranched alkyl of 1 to 6 carbon atoms or cycloalkyl of 3 to 6 carbon atoms wherein said alkyl or cycloalkyl group may optionally be substituted with:

(i) a group of the formula —OR$^{30}$, wherein R$^{30}$ is a hydrogen atom, or an alkyl or acyl group of 1 to 6 carbon atoms, (ii) a group of the formula —NR$^{31}$R$^{32}$, wherein R$^{31}$ and R$^{32}$ are each, independently, a hydrogen atom, alkyl of 1 to 6 carbon atoms, or acyl of 1 to 6 carbon atoms, or (C) a group of the formula —OR$^{33}$, wherein R$^{33}$ is a hydrogen atom, or an alkyl or acyl group of 1 to 6 carbon atoms;

R$^4$ is Cl or trifluoromethyl;

X is =N— or =CR$^5$—, wherein R$^5$ is a hydrogen, fluorine, chlorine, bromine or iodine atom, methyl or trifluoromethyl;

R$^6$ is a hydrogen, fluorine, chlorine, bromine or iodine atom, methyl, cyano, nitro or trifluoromethyl, with the condition that when X is N or =CH—, R$^6$ is chlorine or trifluoromethyl, R$^7$, R$^8$ and R$^9$ are each, independently:

(A) a hydrogen atom, (B) an oxo group, or (C) R$^{34}$, OR$^{34}$, NHR$^{34}$, COR$^{34}$, CONHR$^{34}$, COOR$^{34}$, SO$_2$R$^{34}$, or SR$^{34}$ wherein R$^{34}$ is defined as:

(i) A hydrogen atom, (ii) branched or unbranched alkyl of 1 to 6 carbon atoms or cycloalkyl of 3 to 6 carbon atoms, which alkyl or cycloakyl group may be mono- or polysubstituted with:

(a) halogen, (b) oxo, (c) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:

(1) alkyl of 1 to 3 carbon atoms, (2) —COOH, (3) —SO$_2$OH, (4) —PO(OH)$_2$, (5) a group of the formula —COOR$^{35}$, wherein R$^{35}$ is straight or branched alkyl of 1 to 5 carbon atoms or cycloalkyl of 3 to 5 carbon atoms, (6) a group of the formula —NR$^{36}$R$^{37}$, wherein R$^{36}$ and R$^{37}$ are each independently a hydrogen atom, alkyl of 1 to 6 carbon atoms, cycloalkyl of 3 to 6 carbon atoms or acyl of 1 to 7 carbon atoms, or wherein R$^{36}$ and R$^{37}$ constitute a saturated hydrocarbon bridge of 3 to 5 carbon atoms which together with the nitrogen atom between them form a heterocyclic ring, (7) a group of the formula —CONR$^{38}$R$^{39}$, wherein R$^{38}$ and R$^{39}$ are each independently a hydrogen atom, alkyl of 1 to 6 carbon atoms or cycloalkyl of 3 to 6 carbon atoms, or wherein R$^{38}$ and R$^{39}$ constitute a saturated hydrocarbon bridge of 3 to 5 carbon atoms which together with the nitrogen atom between them form a heterocyclic ring, (8) a group of the formula —OR$^{40}$, wherein R$^{40}$ is a hydrogen atom, or an alkyl or acyl group of 1 to 7 carbon atoms, (9) a group of the formula —SR$^{41}$, wherein R$^{41}$ is a hydrogen atom, or an alkyl or acyl group of 1 to 7 carbon atoms,

(10) cyano,or

(11) an amidino group of the formula

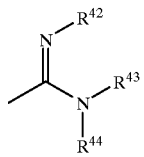

wherein $R^{42}$, $R^{43}$ and $R^{44}$ are each, independently, a hydrogen atom or alkyl of 1 to 3 carbon atoms and wherein two of $R^{42}$, $R^{43}$ and $R^{44}$ may additionally constitute a saturated hydrocarbon bridge of 3 to 5 carbon atoms which together with the nitrogen atom(s) between them form a heterocyclic ring, (d) a group of the formula —COOR$^{45}$, wherein $R^{45}$ is straight or branched alkyl of 1 to 7 carbon atoms or cycloalkyl of 3 to 6 carbon atoms, (e) cyano, (f) a group of the formula —CONR$^{46}$R$^{47}$, wherein $R^{46}$ and $R^{47}$ are each, independently, a hydrogen atom, alkyl of 1 to 6 carbon atoms or cycloalkyl of 3 to 6 carbon atoms, or wherein $R^{46}$ and $R^{47}$ constitute a saturated hydrocarbon bridge of 3 to 5 carbon atoms which together with the nitrogen atom between them form a heterocyclic ring, (g) a group of the formula —OR$^{48}$, wherein $R^{48}$ is a hydrogen atom, or an alkyl or acyl group of 1 to 7 carbon atoms, (h) a group of the formula —SR$^{49}$, wherein $R^{49}$ is a hydrogen atom, or an alkyl or acyl group of 1 to 7 carbon atoms, (i) a group of the formula —NR$^{50}$R$^{51}$, wherein $R^{50}$ and $R^{51}$ are each, independently,
  (1) a hydrogen atom,
  (2) alkyl or acyl of 1 to 7 carbon atoms or cycloalkyl of 3 to 7 carbon atoms,
  (3) a group of the formula —(CH$_2$)$_t$COOH, wherein t is 0, 1 or 2, or
  (4) a group of the formula —(CH$_2$)$_u$COOR$^{52}$, wherein u is 0, 1 or 2, wherein $R^{52}$ is straight or branched alkyl of 1 to 6 carbon atoms,
  or wherein $R^{50}$ and $R^{51}$ constitute a saturated hydrocarbon bridge of 3 to 5 carbon atoms which together with the nitrogen atom between them form a heterocyclic ring, or (j) a quaternary group of the formula

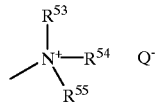

wherein $R^{53}$, $R^{54}$ and $R^{55}$ are each, independently, a branched or unbranched alkyl group of 1 to 7 carbon atoms and Q- is a chlorine, bromine or iodine counterion, (iii) a branched or unbranched carboxylic acid group of 2 to 6 carbon atoms, (iv) a branched or unbranched phosphonic acid group of 2 to 6 carbon atoms, (v) a branched or unbranched sulfonic acid group of 2 to 6 carbon atoms, (vi) an amidino group of the formula

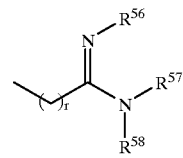

wherein r is 2, 3, 4, 5 or 6, and $R^{56}$, $R^{57}$ and $R^{58}$ are each, independently, a hydrogen atom or alkyl of 1 to 3 carbon atoms, and wherein two of $R^{56}$, $R^{57}$ and $R^{58}$ may additionally constitute a saturated hydrocarbon bridge of 3 to 5 carbon atoms which together with the nitrogen atom(s) between them form a heterocyclic ring, (vii) a guanidino group of the formula

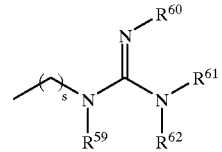

wherein s is 2, 3, 4, 5 or 6, and
$R^{59}$, $R^{60}$, $R^{61}$ and $R^{62}$ are each, independently, a hydrogen atom or alkyl of 1 to 3 carbon atoms, and wherein two of $R^{59}$, $R^{60}$, $R^{61}$ and $R^{62}$ may additionally constitute a saturated hydrocarbon bridge of 3 to 5 carbon atoms which together with the nitrogen atom(s) between them form a heterocyclic ring, (viii) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
wherein one or more hydrogen atoms of said aryl group may be optionally and independently replaced with:
(a) alkyl of 1 to 3 carbon atoms,
(b) —COOH,
(c) —SO$_2$OH,
(d) —PO(OH)$_2$,
(e) a group of the formula —COOR$^{63}$, wherein $R^{63}$ is straight or branched alkyl of 1 to 5 carbon atoms or cycloalkyl of 3 to 5 carbon atoms,
(f) a group of the formula —NR$^{64}$R$^{65}$, wherein $R^{64}$ and $R^{65}$ are each, independently, a hydrogen atom, alkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring,
(g) a group of the formula —CONR$^{66}$R$^{67}$, wherein $R^{66}$ and $R^{67}$ are each, independently, a hydrogen atom, alkyl of 1 to 6 carbon atoms or cycloalkyl of 3 to 6 carbon atoms, or wherein $R^{66}$ and $R^{67}$ constitute a saturated hydrocarbon bridge of 3 to 5 carbon atoms which together with the nitrogen atom between them form a heterocyclic ring,
(h) a group of the formula —OR$^{68}$, wherein R$^{68}$ is a hydrogen atom, or an alkyl or acyl group of 1 to 7 carbon atoms,
(i) a group of the formula —SR$^{69}$, wherein R$^{69}$ is a hydrogen atom, or an alkyl or acyl group of 1 to 7 carbon atoms,
(j) cyano,
(k) or, an amidino group of the formula

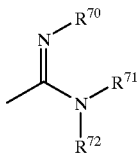

wherein R$^{70}$, R$^{71}$ and R$^{72}$ are each, independently, a hydrogen atom or alkyl of 1 to 3 carbon atoms, and wherein two of R$^{70}$, R$^{71}$ and R$^{72}$ may additionally constitute a saturated hydrocarbon bridge of 3 to 5 carbon atoms which together with the nitrogen atom(s) between them form a heterocyclic ring;
with the proviso that R$^{1}$ and R$^{2}$ are in the trans configuration. and pharmaceutically acceptable salts thereof.

Preferred are compounds of the formula I, wherein:
m is 0 or 1,
n is 0 or 1, and
m+n is equal to either 1 or 2;
Y is an oxygen or sulfur atom;
Z is an oxygen or sulfur atom;
R$^{1}$ is:
  (A) a hydrogen atom, or
  (B) branched or unbranched alkyl of 1 to 3 carbon atoms or cycloalkyl of 3 to 5 carbon atoms wherein said alkyl or cycloalkyl group may optionally be substituted with:
    (i) a group of the formula —OR$^{10}$, wherein R$^{10}$ is an alkyl or acyl group of 1 to 2 carbon atoms,
    (ii) a group of the formula —NR$^{11}$R$^{12}$, wherein R$^{11}$ and R$^{12}$ are each, independently, alkyl of 1 to 2 carbon atoms, or acyl of 1 to 2 carbon atoms, or
  (C) a group of the formula —OR$^{13}$, wherein R$^{13}$ is a an alkyl or acyl group of 1 to 2 carbon atoms;
R$^{2}$ is:
  aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benztiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
  wherein one or more of the hydrogen atoms of said aryl group may be optionally and independently replaced with:

(i) R$^{14}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benztiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said R$^{14}$ aryl group may be optionally and independently replaced with:
  (a) branched or unbranched alkyl of 1 to 6 carbon atoms or cycloalkyl of 3 to 6 carbon atoms, which alkyl or cycloakyl group may be mono- or polysubstituted with halogen or oxo,
  (b) a group of the formula —COOR$^{15}$, wherein R$^{15}$ is straight or branched alkyl of 1 to 5 carbon atoms or cycloalkyl of 3 to 5 carbon atoms,
  (c) a group of the formula —NR$^{16}$R$^{17}$, wherein R$^{16}$ and R$^{17}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{16}$ and R$^{17}$ constitute a saturated hydrocarbon bridge of 3 to 5 carbon atoms which together with the nitrogen atom between them form a heterocyclic ring,
  (d) a group of the formula —CONR$^{18}$R$^{19}$, wherein R$^{18}$ and R$^{19}$ are each independently a hydrogen atom, alkyl or fluoroalkyl of 1 to 6 carbon atoms or cycloalkyl of 3 to 6 carbon atoms, or wherein R$^{18}$ and R$^{19}$ constitute a saturated hydrocarbon bridge of 3 to 5 carbon atoms which together with the nitrogen atom between them form a heterocyclic ring,
  (e) a group of the formula —OR$^{20}$, wherein R$^{20}$ is a hydrogen atom, or an alkyl, fluoroalkyl or acyl group of 1 to 7 carbon atoms,
  (f) a group of the formula —SR$^{21}$, wherein R$^{21}$ is a hydrogen atom, or an alkyl, fluoroalkyl or acyl group of 1 to 7 carbon atoms,
  (g) cyano,
  (h) nitro,
  (i) halogen,
(ii) methyl, which may be mono- or polysubstituted with fluorine atoms,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —COOR$^{22}$, wherein R$^{22}$ is straight or branched alkyl of 1 to 5 carbon atoms or cycloalkyl of 3 to 5 carbon atoms,
(v) a group of the formula —NR$^{23}$R$^{24}$, wherein R$^{23}$ and R$^{24}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{23}$ and R$^{24}$ constitute a saturated hydrocarbon bridge of 3 to 5 carbon atoms which together with the nitrogen atom between them form a heterocyclic ring,
(vi) a group of the formula —CONR$^{25}$R$^{26}$, wherein R$^{25}$ and R$^{26}$ are each, independently, a hydrogen atom, alkyl or fluoroalkyl of 1 to 6 carbon atoms or cycloalkyl of 3 to 6 carbon atoms, or wherein R$^{25}$ and R$^{26}$ constitute a saturated hydrocarbon bridge of 3 to 5 carbon atoms which together with the nitrogen atom between them form a heterocyclic ring,
(vii) a group of the formula —COR$^{27}$, wherein R$^{27}$ is a hydrogen atom, straight or branched alkyl of 1 to 5 carbon atoms, or cycloalkyl of 3 to 5 carbon atoms,
(viii) a group of the formula —OR$^{28}$, wherein R$^{28}$ is a hydrogen atom, an alkyl, fluoroalkyl or acyl group of 1 to 7 carbon atoms,
(ix) a group of the formula —SR$^{29}$, wherein R$^{29}$ is a hydrogen atom, an alkyl, fluoroalkyl or acyl group of 1 to 7 carbon atoms,
(x) cyano,
(xi) nitro, or
(xii) halogen, R$^3$ is:
(A) a hydrogen atom,
(B) methyl, or
(C) a group of the formula —OR$^{33}$, wherein R$^{33}$ is a hydrogen atom methyl;

R$^4$ is Cl or trifluoromethyl;
X is =N— or =—OR$^5$—,
wherein R$^5$ is a hydrogen, fluorine, chlorine, bromine or iodine atom, methyl or trifluoromethyl;
R$^6$ is a hydrogen, fluorine, chlorine, bromine or iodine atom, methyl, cyano, nitro or trifluoromethyl, with the condition that when X is N or =CH—, R$^6$ is chlorine or trifluoromethyl;

R$^7$, R$^8$ and R$^9$ are each, independently:
(A) a hydrogen atom,
(B) an oxo group, or
(C) R$^{34}$, OR$^{34}$, NHR$^{34}$, COR$^{34}$, CONHR$^{34}$, COOR$^{34}$, SO$_2$R$^{34}$, or SR$^{34}$
wherein R$^{34}$ is defined as:
(i) a hydrogen atom,
(ii) branched or unbranched alkyl of 1 to 6 carbon atoms or cycloalkyl of 3 to 6 carbon atoms, which alkyl or cycloakyl group may be mono- or polysubstituted with:
(a) oxo,
(b) phenyl,
wherein one or more hydrogen atoms of said phenyl group may be optionally and independently replaced with:
(1) alkyl of 1 to 3 carbon atoms,
(2) —COOH,
(3) —SO$_2$OH,
(4) —PO(OH)$_2$,
(5) a group of the formula —COOR$^{35}$, wherein R$^{35}$ is straight or branched alkyl of 1 to 5 carbon atoms or cycloalkyl of 3 to 5 carbon atoms,
(6) a group of the formula —NR$^{36}$R$^{37}$, wherein R$^{36}$ and R$^{37}$ are each independently a hydrogen atom, alkyl of 1 to 6 carbon atoms, cycloalkyl of 3 to 6 carbon atoms or acyl of 1 to 7 carbon atoms, or wherein R$^{36}$ and R$^{37}$ constitute a saturated hydrocarbon bridge of 3 to 5 carbon atoms which together with the nitrogen atom between them form a heterocyclic ring,
(7) a group of the formula —CONR$^{38}$R$^{39}$, wherein R$^{38}$ and R$^{39}$ are each independently a hydrogen atom, alkyl of 1 to 6 carbon atoms or cycloalkyl of 3 to 6 carbon atoms, or wherein R$^{38}$ and R$^{39}$ constitute a saturated hydrocarbon bridge of 3 to 5 carbon atoms which together with the nitrogen atom between them form a heterocyclic ring,
(8) a group of the formula —OR$^{40}$, wherein R$^{40}$ is a hydrogen atom, or an alkyl or acyl group of 1 to 7 carbon atoms,
(9) a group of the formula —SR$^{41}$, wherein R$^{41}$ is a hydrogen atom, or an alkyl or acyl group of 1 to 7 carbon atoms,
(10) cyano,or
(11) an amidino group of the formula

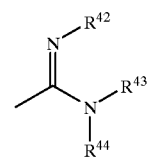

wherein R$^{42}$, R$^{43}$ and R$^{44}$ are each, independently, a hydrogen atom or alkyl of 1 to 3 carbon atoms and wherein two of R$^{42}$, R$^{43}$ and R$^{44}$ may additionally constitute a saturated hydrocarbon bridge of 3 to 5 carbon atoms which together with the nitrogen atom(s) between them form a heterocyclic ring,
(c) a group of the formula —COOR$^{45}$, wherein R$^{45}$ is straight or branched alkyl of 1 to 7 carbon atoms or cycloalkyl of 3 to 6 carbon atoms,
(d) cyano,
(e) a group of the formula —CONR$^{46}$R$^{47}$, wherein R$^{46}$ and R$^{47}$ are each, independently, a hydrogen atom, alkyl of 1 to 6 carbon atoms or cycloakyl of 3 to 6 carbon atoms, or wherein R$^{46}$ and R$^{47}$ constitute a saturated hydrocarbon bridge of 3 to 5 carbon atoms which together with the nitrogen atom between them form a heterocyclic ring,
(f) a group of the formula —OR$^{48}$, wherein R$^{48}$ is a hydrogen atom, or an alkyl or acyl group of 1 to 7 carbon atoms,
(g) a group of the formula —SR$^{49}$, wherein R$^{49}$ is a hydrogen atom, or an alkyl or acyl group of 1 to 7 carbon atoms,
(h) a group of the formula —NR$^{50}$R$^{51}$, wherein R$^{50}$ and R$^{51}$ are each, independently,
(1) a hydrogen atom,
(2) alkyl or acyl of 1 to 7 carbon atoms or cycloalkyl of 3 to 7 carbon atoms,
(3) a group of the formula —CH$_2$)$_t$COOH, wherein t is 0, 1or 2, or
(4) a group of the formula —(CH$_2$)$_u$COOR$^{52}$, wherein u is 0, 1 or 2, wherein R$^{52}$ is straight or branched alkyl of 1 to 6 carbon atoms,
or wherein R$^{50}$ and R$^{51}$ constitute a saturated hydrocarbon bridge of 3 to 5 carbon atoms which together with the nitrogen atom between them form a heterocyclic ring, or

13

(i) a quaternary group of the formula

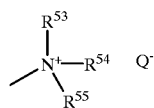

wherein $R^{53}$, $R^{54}$ and $R^{55}$ are each, independently, a branched or unbranched alkyl group of 1 to 7 carbon atoms and $Q^-$ is a chlorine, bromine or iodine counterion,
(iii) a branched or unbranched carboxylic acid group of 2 to 6 carbon atoms,
(iv) a branched or unbranched phosphonic acid group of 2 to 6 carbon atoms,
(v) a branched or unbranched sulfonic acid group of 2 to 6 carbon atoms,
(vi) an amidino group of the formula

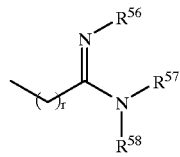

wherein r is 2, 3, 4, 5 or 6, and
$R^{56}$, $R^{57}$ and $R^{58}$ are each, independently, a hydrogen atom or alkyl of 1 to 3 carbon atoms, and wherein two of $R^{56}$, $R^{57}$ and $R^{58}$ may additionally constitute a saturated hydrocarbon bridge of 3 to 5 carbon atoms which together with the nitrogen atom(s) between them form a heterocyclic ring,
(vii) a guanidino group of the formula

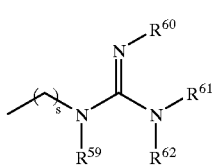

wherein s is 2, 3, 4, 5 or 6, and
$R^{59}$, $R^{60}$, $R^{61}$ and $R^{62}$ are each, independently, a hydrogen atom or alkyl of 1 to 3 carbon atoms, and wherein two of $R^{59}$, $R^{60}$, $R^{61}$ and $R^{62}$ may additionally constitute a saturated hydrocarbon bridge of 3 to 5 carbon atoms which together with the nitrogen atom(s) between them form a heterocyclic ring,
(viii) phenyl,
wherein one or more hydrogen atoms of said phenyl group may be optionally and independently replaced with:
(a) alkyl of 1 to 3 carbon atoms,
(b) —COOH,
(c) —SO$^2$OH,
(d) —PO(OH)$_2$,
(e) a group of the formula —COOR$^{63}$, wherein R$^{63}$ is straight or branched alkyl of 1 to 5 carbon atoms or cycloalkyl of 3 to 5 carbon atoms,
(f) a group of the formula —NR$^{64}$R$^{65}$, wherein R$^{64}$ and R$^{65}$ are each, independently, a hydrogen atom, alkyl of 1 to 6 carbon atoms, cycloalkyl of 3 to 6 carbon atoms or acyl of 1 to 7 carbon atoms, or wherein R$^{64}$ and R$^{65}$ constitute a saturated hydro-

14 carbon bridge of 3 to 5 carbon atoms which together with the nitrogen atom between them form a heterocyclic ring,
(g) a group of the formula —CONR$^{66}$R$^{67}$, wherein R$^{66}$ and R$^{67}$ are each, independently, a hydrogen atom, alkyl of 1 to 6 carbon atoms or cycloalkyl of 3 to 6 carbon atoms, or wherein R$^{66}$ and R$^{67}$ constitute a saturated hydrocarbon bridge of 3 to 5 carbon atoms which together with the nitrogen atom between them form a heterocyclic ring,
(h) a group of the formula —OR$^{68}$, wherein R$^{68}$ is a hydrogen atom, or an alkyl or acyl group of 1 to 7 carbon atoms,
(i) a group of the formula —SR$^{69}$, wherein R$^{69}$ is a hydrogen atom, or an alkyl or acyl group of 1 to 7 carbon atoms,
(j) cyano,
(k) or, an amidino group of the formula

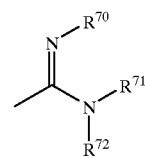

wherein $R^{70}$, $R^{71}$ and $R^{72}$ are each, independently, a hydrogen atom or alkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring;
with the proviso that $R^1$ and $R^2$ are in the trans configuration;
and pharmaceutically acceptable salts thereof.
More preferred are compounds of the formula I, wherein:
m is 0 or 1,
n is 0 or 1, and
m+n is equal to either 1 or 2;
Y is an oxygen atom;
Z is an oxygen atom;
$R^1$ is:
(A) a hydrogen atom,
(B) methyl, or
(C) a group of the formula —OR$^{13}$, wherein R$^{13}$ is a an alkyl or acyl group of 1 to 2 carbon atoms;
$R^2$ is:
phenyl,
wherein one or more of the hydrogen atoms of said phenyl group may be optionally and independently replaced with:
(i) R$^{14}$, which is aryl selected from the class consisting of phenyl, 3-pyridyl, or 5-pyrimidinyl,
wherein one or more of the hydrogen atoms of said R$^{14}$ aryl group may be optionally and independently replaced with:
(a) methyl,
(b) cyano,
(c) nitro, or
(d) halogen,
(ii) methyl, which may be mono- or polysubstituted with fluorine atoms,
(iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —COOR$^{22}$, wherein R$^{22}$ is straight or branched alkyl of 1 to 5 carbon atoms or cycloalkyl of 3 to 5 carbon atoms, (v) a group of the formula —CONR$^{25}$R$^{26}$, wherein R$^{25}$ and R$^{26}$ are each, independently, a hydrogen atom, alkyl or fluoroalkyl of 1 to 6 carbon atoms or cycloalkyl of 3 to 6 carbon atoms, or wherein R$^{25}$ and R$^{26}$ constitute a saturated hydrocarbon bridge of 3 to 5 carbon atoms which together with the nitrogen atom between them form a heterocyclic ring, (vi) a group of the formula —COR$^{27}$, wherein R$^{27}$ is a hydrogen atom, straight or branched alkyl of 1 to 5 carbon atoms, or cycloalkyl of 3 to 5 carbon atoms, (vii) a group of the formula —OR$^{28}$, wherein R$^{28}$ is a hydrogen atom, an alkyl, fluoroalkyl or acyl group of 1 to 7 carbon atoms, (viii) a group of the formula —SR$^{29}$, wherein R$^{29}$ is a hydrogen atom, an alkyl, fluoroalkyl or acyl group of 1 to 7 carbon atoms, (ix) cyano, (x) nitro, or (xi) halogen, R$^3$ is:

(A) a hydrogen atom, (B) methyl, or (C) a group of the formula —OR$^{33}$, wherein R$^{33}$ is a hydrogen atom methyl;

R$^4$ is Cl or trifluoromethyl;

X is =N— or =—OR$^5$—, wherein R$^5$ is a hydrogen, fluorine, chlorine, bromine or iodine atom, methyl or trifluoromethyl;

R$^6$ is a hydrogen, fluorine, chlorine, bromine or iodine atom, methyl, cyano, nitro or trifluoromethyl, with the condition that when X is N or =CH—, R$^6$ is chlorine or trifluoromethyl;

R$^7$, R$^8$ and R$^9$ are each, independently:

(A) a hydrogen atom, (B) an oxo group, or (C) R$^{34}$, OR$^{34}$, NHR$^{34}$, COR$^{34}$, CONHR$^{34}$, COOR$^{34}$, SO$_2$R$^{34}$, or SR$^{34}$ wherein R$^{34}$ is defined as:

(i) a hydrogen atom, (ii) branched or unbranched alkyl of 1 to 6 carbon atoms or cycloalkyl of 3 to 6 carbon atoms, which alkyl or cycloakyl group may be mono- or polysubstituted with:

(a) oxo, (b) phenyl, wherein one or more hydrogen atoms of said phenyl group may be optionally and independently replaced with:

(1) alkyl of 1 to 3 carbon atoms, (2) —COOH, (3) —SO$_2$OH, (4) —PO(OH)$_2$, (5) a group of the formula —COOR$^{35}$, wherein R$^{35}$ is straight or branched alkyl of 1 to 5 carbon atoms or cycloalkyl of 3 to 5 carbon atoms, (6) a group of the formula —NR$^{36}$R$^{37}$, wherein R$^{36}$ and R$^{37}$ are each independently a hydrogen atom, alkyl of 1 to 6 carbon atoms, cycloalkyl of 3 to 6 carbon atoms or acyl of 1 to 7 carbon atoms, or wherein R$^{36}$ and R$^{37}$ constitute a saturated hydrocarbon bridge of 3 to 5 carbon atoms which together with the nitrogen atom between them form a heterocyclic ring, (7) a group of the formula —CONR$^{38}$R$^{39}$, wherein R$^{38}$ and R$^{39}$ are each independently a hydrogen atom, alkyl of 1 to 6 carbon atoms or cycloalkyl of 3 to 6 carbon atoms, or wherein R$^{38}$ and R$^{39}$ constitute a saturated hydrocarbon bridge of 3 to 5 carbon atoms which together with the nitrogen atom between them form a heterocyclic ring, (8) a group of the formula —OR$^{40}$, wherein R$^{40}$ is a hydrogen atom, or an alkyl or acyl group of 1 to 7 carbon atoms, (9) a group of the formula —SR$^{41}$, wherein R$^{41}$ is a hydrogen atom, or an alkyl or acyl group of 1 to 7 carbon atoms,

(10) cyano, or

(11) an amidino group of the formula

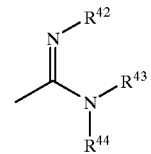

wherein R$^{42}$, R$^{43}$ and R$^{44}$ are each, independently, a hydrogen atom or alkyl of 1 to 3 carbon atoms and wherein two of R$^{42}$, R$^{43}$ and R$^{44}$ may additionally constitute a saturated hydrocarbon bridge of 3 to 5 carbon atoms which together with the nitrogen atom(s) between them form a heterocyclic ring, (c) a group of the formula —COOR$^{45}$, wherein R$^{45}$ is straight or branched alkyl of 1 to 7 carbon atoms or cycloalkyl of 3 to 6 carbon atoms, (d) cyano, (e) a group of the formula —CONR$^{46}$R$^{47}$, wherein R$^{46}$ and R$^{47}$ are each, independently, a hydrogen atom, alkyl of 1 to 6 carbon atoms or cycloalkyl of 3 to 6 carbon atoms, or wherein R$^{46}$ and R$^{47}$ constitute a saturated hydrocarbon bridge of 3 to 5 carbon atoms which together with the nitrogen atom between them form a heterocyclic ring, (f) a group of the formula —OR$^{48}$, wherein R$^{48}$ is a hydrogen atom, or an alkyl or acyl group of 1 to 7 carbon atoms, (g) a group of the formula —SR$^{49}$, wherein R$^{49}$ is a hydrogen atom, or an alkyl or acyl group of 1 to 7 carbon atoms, (h) a group of the formula —NR$^{50}$R$^{51}$, wherein R$^{50}$ and R$^{51}$ are each, independently, (1) a hydrogen atom, (2) alkyl or acyl of 1 to 7 carbon atoms or cycloalkyl of 3 to 7 carbon atoms, (3) a group of the formula —CH$_2$)$_t$COOH, wherein t is 0, 1 or 2, or (4) a group of the formula —(CH$_2$)$_u$COOR$^{52}$, wherein u is 0, 1 or 2, wherein R$^{52}$ is straight or branched alkyl of 1 to 6 carbon atoms, or wherein R$^{50}$ and R$^{51}$ constitute a saturated hydrocarbon bridge of 3 to 5 carbon atoms which together with the nitrogen atom between them form a heterocyclic ring, or (i) a quaternary group of the formula

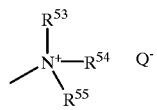

wherein $R^{53}$, $R^{54}$ and $R^{55}$ are each, independently, a branched or unbranched alkyl group of 1 to 7 carbon atoms and $Q^-$ is a chlorine, bromine or iodine counterion,
(iii) a branched or unbranched carboxylic acid group of 2 to 6 carbon atoms,
(iv) a branched or unbranched phosphonic acid group of 2 to 6 carbon atoms,
(v) a branched or unbranched sulfonic acid group of 2 to 6 carbon atoms,
(vi) an amidino group of the formula

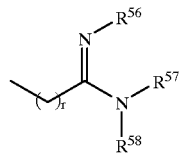

wherein r is 2, 3, 4, 5 or 6, and $R^{56}$, $R^{57}$ and $R^{58}$ are each, independently, a hydrogen atom or alkyl of 1 to 3 carbon atoms, and wherein two of $R^{56}$, $R^{57}$ and $R^{58}$ may additionally constitute a saturated hydrocarbon bridge of 3 to 5 carbon atoms which together with the nitrogen atom(s) between them form a heterocyclic ring,
(vii) a guanidino group of the formula

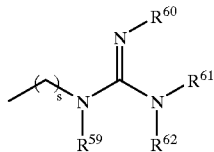

wherein s is 2, 3, 4, 5 or 6, and $R^{59}$, $R^{60}$, $R^{61}$ and $R^{62}$ are each, independently, a hydrogen atom or alkyl of 1 to 3 carbon atoms, and wherein two of $R^{59}$, $R^{60}$, $R^{61}$ and $R^{62}$ may additionally constitute a saturated hydrocarbon bridge of 3 to 5 carbon atoms which together with the nitrogen atom(s) between them form a heterocyclic ring,
(viii) phenyl,
wherein one or more hydrogen atoms of said phenyl group may be optionally and independently replaced with:
(a) alkyl of 1 to 3 carbon atoms,
(b) —COOH,
(c) —SO$_2$OH,
(d) —PO(OH)$_2$,
(e) a group of the formula —COOR$^{63}$, wherein R$^{63}$ is straight or branched alkyl of 1 to 5 carbon atoms or cycloalkyl of 3 to 5 carbon atoms,
(f) a group of the formula —NR$^{64}$R$^{65}$, wherein R$^{64}$ and R$^{65}$ are each, independently, a hydrogen atom, alkyl of 1 to 6 carbon atoms, cycloalkyl of 3 to 6 carbon atoms or acyl of 1 to 7 carbon atoms, or wherein R$^{64}$ and R$^{65}$ constitute a saturated hydrocarbon bridge of 3 to 5 carbon atoms which together with the nitrogen atom between them form a heterocyclic ring,
(g) a group of the formula —CONR$^{66}$R$^{67}$, wherein R$^{66}$ and R$^{67}$ are each, independently, a hydrogen atom, alkyl of 1 to 6 carbon atoms or cycloalkyl of 3 to 6 carbon atoms, or wherein R$^{66}$ and R$^{67}$ constitute a saturated hydrocarbon bridge of 3 to 5 carbon atoms which together with the nitrogen atom between them form a heterocyclic ring,
(h) a group of the formula —OR$^{68}$, wherein R$^{68}$ is a hydrogen atom, or an alkyl or acyl group of 1 to 7 carbon atoms,
(i) a group of the formula —SR$^{69}$, wherein R$^{69}$ is a hydrogen atom, or an alkyl or acyl group of 1 to 7 carbon atoms,
(j) cyano,
(k) or, an amidino group of the formula

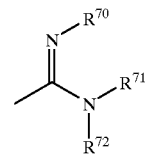

wherein $R^{70}$, $R^{71}$ and $R^{72}$ are each, independently, a hydrogen atom or alkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring;
with the proviso that $R^1$ and $R^2$ are in the trans configuration;
and pharmaceutically acceptable salts thereof.

Even more preferred are compounds of the formula I, wherein:
m is 0 or 1,
n is 0 or 1, and
m+n is equal to either 1 or 2;
Y is an oxygen atom;
Z is an oxygen atom;
$R^1$ is:
 (A) a hydrogen atom, or
 (B) methyl;
$R^2$ is:
 phenyl,
  wherein one or more of the hydrogen atoms of said phenyl group may be optionally and independently replaced with:
  (i) $R^{14}$, which is aryl selected from the class consisting of phenyl, 3-pyridyl, or 5-pyrimidinyl,
   wherein one or more of the hydrogen atoms of said $R^{14}$ aryl group may be optionally and independently replaced with:
    (a) methyl,
    (b) cyano,
    (c) nitro, or
    (d) halogen,
  (ii) cyano,
  (iii) nitro, or
  (iv) halogen;
$R^3$ is a hydrogen atom;
$R^4$ is Cl;
X is =CH—;

$R^6$ is Cl;
$R^7$, $R^8$ and $R^9$ are each, independently:
(A) a hydrogen atom,
(B) an oxo group, or
(C) $R^{34}$ or $-OR^{34}$,
  wherein $R^{34}$ is defined as:
  (i) a hydrogen atom,
  (ii) branched or unbranched alkyl of 1 to 6 carbon atoms or cycloalkyl of 3 to 6 carbon atoms, which alkyl or cycloakyl group may be mono- or polysubstituted with:
    (a) oxo,
    (b) phenyl,
      wherein one or more hydrogen atoms of said phenyl group may be optionally and independently replaced with:
      (1) alkyl of 1 to 3 carbon atoms,
      (2) —COOH,
      (3) a group of the formula $-NR^{36}R^{37}$, wherein $R^{36}$ and $R^{37}$ are each independently a hydrogen atom, alkyl of 1 to 6 carbon atoms, cycloalkyl of 3 to 6 carbon atoms or acyl of 1 to 7 carbon atoms, or wherein $R^{36}$ and $R^{37}$ constitute a saturated hydrocarbon bridge of 3 to 5 carbon atoms which together with the nitrogen atom between them form a heterocyclic ring,
      (4) a group of the formula $-OR^{40}$, wherein $R^{40}$ is a hydrogen atom, or an alkyl or acyl group of 1 to 7 carbon atoms, or
      (5) an amidino group of the formula

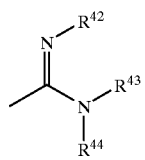

wherein $R^{42}$, $R^{43}$ and R44 are each, independently, a hydrogen atom or alkyl of 1 to 3 carbon atoms and wherein two of $R^{42}$, $R^{43}$ and $R^{44}$ may additionally constitute a saturated hydrocarbon bridge of 3 to 5 carbon atoms which together with the nitrogen atom(s) between them form a heterocyclic ring,
    (c) a group of the formula $-OR^{48}$, wherein $R^{48}$ is a hydrogen atom, or an alkyl or acyl group of 1 to 7 carbon atoms,
    (d) a group of the formula $-NR^{50}R^{51}$, wherein $R^{50}$ and $R^{51}$ are each, independently,
      (1) a hydrogen atom,
      (2) alkyl or acyl of 1 to 7 carbon atoms or cycloalkyl of 3 to 7 carbon atoms, or
      (3) a group of the formula $-(CH_2)_tCOOH$, wherein t is 0, 1 or 2,
      or wherein $R^{50}$ and $R^{51}$ constitute a saturated hydrocarbon bridge of 3 to 5 carbon atoms which together with the nitrogen atom between them form a heterocyclic ring, or
  (iii) a branched or unbranched carboxylic acid group of 2 to 6 carbon atoms,
  (iv) an amidino group of the formula

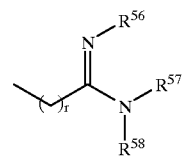

wherein r is 2, 3, 4, 5 or 6, and $R^{56}$, $R^{57}$ and $R^{58}$ are each, independently, a hydrogen atom or alkyl of 1 to 3 carbon atoms, and wherein two of $R^{56}$, $R^{57}$ and $R^{58}$ may additionally constitute a saturated hydrocarbon bridge of 3 to 5 carbon atoms which together with the nitrogen atom(s) between them form a heterocyclic ring,
  (v) phenyl,
    wherein one or more hydrogen atoms of said phenyl group may be optionally and independently replaced with:
    (a) alkyl of 1 to 3 carbon atoms,
    (b) —COOH,
    (c) a group of the formula $-NR^{64}R^{65}$, wherein $R^{64}$ and $R^{65}$ are each, independently, a hydrogen atom, alkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring,
    (d) a group of the formula $-OR^{68}$, wherein $R^{68}$ is a hydrogen atom, or an alkyl or acyl group of 1 to 7 carbon atoms,
    (e) or, an amidino group of the formula

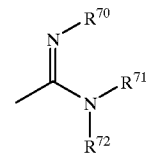

wherein $R^{70}$, $R^{71}$ and $R^{72}$ are each, independently, a hydrogen atom or alkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring;
with the proviso that $R^1$ and $R^2$ are in the trans configuration;
and pharmaceutically acceptable salts thereof.

Further preferred are compounds of the formula I, wherein:
m is 0;
n is 1;
Y is an oxygen atom;
Z is an oxygen atom;
$R^1$ is;
  (A) a hydrogen atom, or
  (B) methyl;
$R^2$ is:
  phenyl,
    wherein one or more of the hydrogen atoms of said phenyl group may be optionally and independently replaced with:

(i) $R^{14}$, which is aryl selected from the class consisting of phenyl, 3-pyridyl, or 5-pyrimidinyl,
(ii) cyano,
(iii) nitro, or
(iv) halogen;

$R^3$ is a hydrogen atom;
$R^4$ is Cl;
X is =CH—;
$R^6$ is Cl;
$R^7$, $R^8$ and $R^9$ are each, independently:
 (A) a hydrogen atom,
 (B) an oxo group, or
 (C) $R^{34}$ or $OR^{34}$,
  wherein $R^{34}$ is defined as:
  (i) a hydrogen atom,
  (ii) branched or unbranched alkyl of 1 to 6 carbon atoms or cycloalkyl of 3 to 6 carbon atoms, which alkyl or cycloakyl group may be mono- or polysubstituted with a group of the formula —$OR^{48}$, wherein $R^{48}$ is a hydrogen atom, or an alkyl of 1 to 7 carbon atoms;

with the proviso that $R^1$ and $R^2$ are in the trans configuration;
and pharmaceutically acceptable salts thereof.

Especially preferred compounds include:

2-(3,5-Dichlorophenyl)-7-(R*)-phenyl-7a-(R*)-tetrahydropyrrolo[1,2-c]imidazole-1,3-dione;

2-(3,5-Dichlorophenyl)-7a-(R*)-methyl-7-(R*)-phenyl-tetrahydropyrrolo[1,2-c]imidazole-1,3-dione;

7-(R*)-(4-Bromophenyl)-2-(3,5-dichlorophenyl)-7a-(R*)-tetrahydropyrrolo[1,2-c]imidazole-1,3-dione;

2-(3,5-dichlorophenyl)-8a-(R*)-methyl-8-(R*)-phenyl-tetrahydroimidazo[1,5-b]pyridine-1,3-dione;

2-(3,5-dichlorophenyl)-8a-(S*)-methoxy-8-(R*)-phenyl-tetrahydroimidazo[1,5-b]pyridine-1,3-dione;

7-(R*)-(4-Bromophenyl)-2-(3,5-dichlorophenyl)-7a-(R*)-methyl-tetrahydropyrrolo[1,2-c]imidazole-1,3-dione, 2-(3,5-dichlorophenyl)-7-(R*)-[4-(3-pyridyl)phenyl]-7a-(R*)methyl-tetrahydropyrrolo[1,2-c]imidazole-1,3-dione;

7-(R*)-(4-Bromophenyl)-2-(3,5-dichlorophenyl)-6-(S*)-hydroxy-7a-(R*)-tetrahydropyrrolo[1,2-c]imidazole-1,3-dione;

7-(R*)-(4-Bromophenyl)-2-(3,5-dichlorophenyl)-7a-(R*)-allyl-tetrahydropyrrolo[1,2-c]imidazole-1,3-dione; and, 7-(R*)-(4-Bromophenyl)-2-(3,5-dichlorophenyl)-5-(S*)-hydroxy-7a-(R*)-methyl-tetrahydropyrrolo[1,2-c]imidazole-1,3-dione;

and pharmaceutically acceptable salts thereof.

In the names of the above-mentioned preferred compounds, the * denotes relative stereochemistry, not absolute stereochemistry.

It will be appreciated that the compounds of formula I have at least one chiral center. Ultimately preferred are those compounds of formula I with the absolute stereochemistry depicted below in formula Ia.

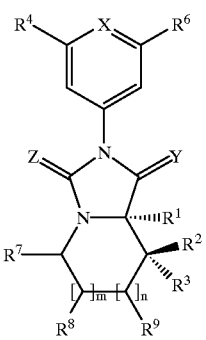

Synthesis of the Compounds of the Invention

The starting amino acids and their derivatives necessary for the synthesis of the compounds of the examples are either commercially available or are produced by obvious modifications of known literature. In particular, the method of Chung et al., *J. Org. Chem.* 1990, 55, 270–275 teaches the synthesis and resolution of 3-substituted proline derivatives. When not obvious, the synthesis of the starting material is described. General methods for the synthesis of compounds of the invention are described below and illustrated in Scheme I.

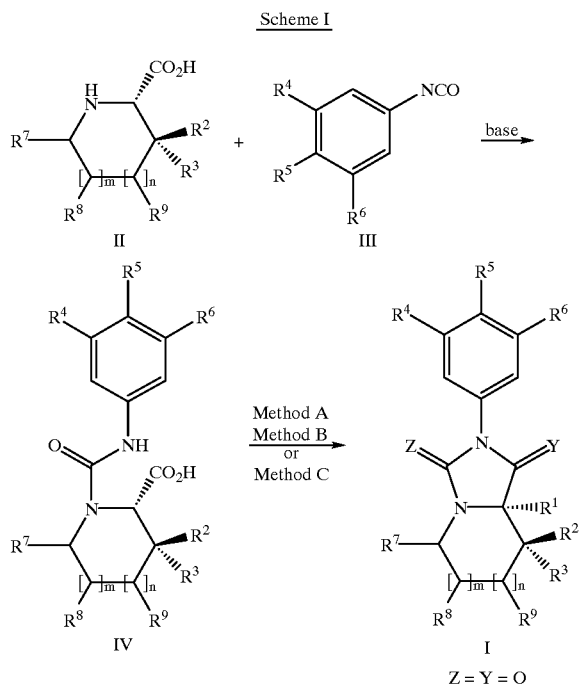

Scheme I

General Method A

Starting with an Amino Acid and a Phenylisocyanate. Cyclization with Acid

An appropriate amino acid is dissolved in aqueous base (such as, for example, NaOH, KOH, $Na_2CO_3$, $NaHCO_3$, $K_2CO_3$ or $KHCO_3$) and warmed to between about 20 and 90° C. An appropriate isocyanate is added to this mixture and the resulting solution was stirred until the reaction essentially reaches completion. Upon cooling, the mixture is acidified and the resulting ureidoacetic acid is isolated by filtration or by extraction into organic solvent. Removal of solvent produces an intermediate which is cyclized by heating in the presence of a catalytic amount of acid (such as, for example, sulfuric acid, methanesulfonic acid, benzenesulfonic acid or hydrochloric acid) in an organic or aqueous solvent, to produce the desired hydantoin. Workup consists of collection of the desired product by filtration and purification by, for example, silica gel chromatography or recrystallization.

General Method B

Starting with an Amino Acid and a Phenylisocyanate. Cyclization with EDC

An appropriate amino acid is dissolved in aqueous base (such as, for example, NaOH, KOH, $Na_2CO_3$, $NaHCO_3$, $K_2CO_3$ or $KHCO_3$) and warmed to between about 20 and 90° C. An appropriate isocyanate is added to this mixture and the resulting solution is stirred until the reaction essentially reaches completion. Upon cooling, the mixture is acidified and the resulting ureidoacetic acid is isolated by filtration or extraction into organic solvent. Removal of solvent produces the intermediate ureidoacetic acid which is then cyclized to the desired product in organic solvent (such as, for example, DMF, NMP, or THF) using any of a number of dehydrating agents (such as, for example, dicyclohexylcarbodiimide (DCC) or 1-(3-dimethylaminopropyl)-3-ethylcarbodiimide HCl (EDC)) in the presence of an activating agent (such as 1-hydroxybenzotriazole hydrate (HOBT)) and a non-nucleophilic base (such as, for example, triethylamine or N,N-diisopropylethylamine). Work up consists of extraction into an organic solvent followed by purification via, for example, silica gel chromatography or recrystallization.

General Method C

Starting with an Amino Ester or a Hydroxy Ester and a Phenylisocyanate. Cyclization with Base or Acid An appropriate amino ester or hydroxy ester and an appropriate isocyanate are dissolved in an organic solvent (such as, for example, DMF, THF or DMSO) in the presence of a base (such as, for example, NaOH, KOH, $Na_2CO_3$, $NaHCO_3$, $K_2CO_3$ or $KHCO_3$) and warmed to between about room temperature and 60° C. After approximately 1 h, the temperature of the reaction mixture is raised to between about 50 and 100° C. until the reaction appears complete. The solution is then cooled and diluted with an organic solvent (such as, for example, EtOAc or $CH_2Cl_2$). The organic phage is washed sequentially with dilute aqueous acid (e.g. 1 NHCl) and water, dried (e.g. over $MgSO_4$)and concentrated. The desired product is purified, for example by silica gel chromatography or by recrystallization. (Alternatively the ureidoacetic ester can be cyclized to the product by heating to between about 50 and 100° C. in the presence of an acid such as, for example, aqueous HCl until the reaction appears complete).

While the above general syntheses are illustrative of examples where X=Z=O, and $R^2$=H, the preparation of other compounds of the invention will be apparent to those skilled in the art, e.g. use of an isothiocyanate in place of an isocyanate will provide compounds where X=S. Examples where $R^3$ is an alkyl group can be prepared by alkylation of a compound where $R^2$=H, as is described below in Examples 2 and 5.

Synthesisis of Specific Compounds of the Examples

Example 1

2-(3,5-Dichlorophenyl-7-R*-phenyl-7a-(R*) tetrahydropyrrolo[1,2-c]imidazole-1,3-dione

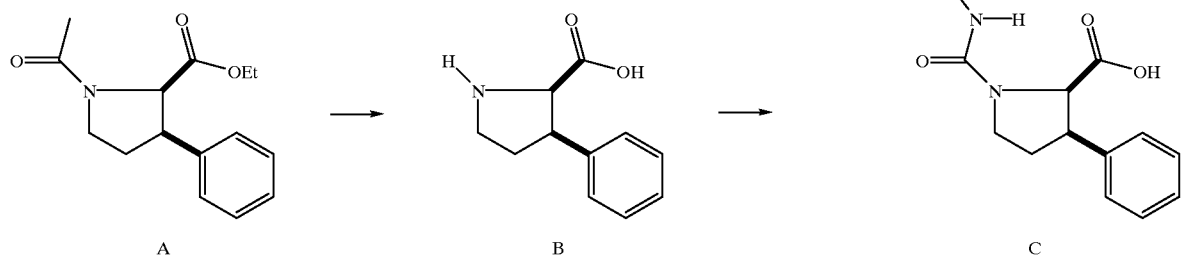

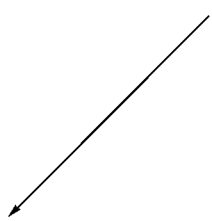

-continued

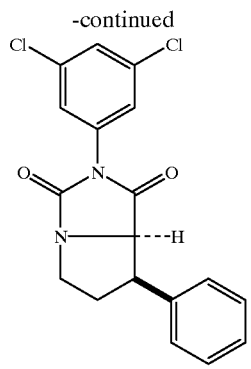

Intermediate A (2.4 g, 9.2 mmol), synthesized by the method of Chung et al., *J. Org. Chem.* 1990, 55, 270–275, was heated to reflux in 25 mL of 6 N HCl for 14 h. The solvents were removed by rotary evaporation to give the HCl salt of the amino acid B, after recrystallization from EtOH/Et$_2$O (1.53 g, 72%). Intermediate B (1,13 g, 9.9 mmol) was then dissolved in 20 mL of water containing two equivalents of NaOH and then treated with 3,5-dichlorophenylisocyanate at 65° C. After 1 h the mixture was cooled and filtered through a 0.45 μm filter. The water filtrate was acidified with concentrated HCl until a precipitate formed. The precipitate was isolated by filtration and dried which provided 960 mg (51%) of intermediate C. Intermediate C (408 mg, 1.07 mmol) was mixed at room temperature with EDC (206.2 mg, 1.07 mmol) and HOBT (145 mg, 1.07 mmol) in 20 mL of DMF for 1 h. N,N-diisopropylethylamine (278 mg, 2.15 mmol) was then added and the mixture was stirred for 18 h. The solution was then diluted with water and extracted three times into CH$_2$Cl$_2$. The organic layer was washed three times with water to remove residual DMF, dried over MgSO$_4$ and purified by silica gel chromatography (3:1 Hexanes:EtOAc) to yield 160 mg (41%) of the title compound (1). Mp 158–159° C.

Example 2

2-(3,5-Dichlorophenyl)-7a-(R*)-methyl-7-(R*)-phenyl-tetrahydropyrrolo[1,2-c]imidazole-1,3-dione

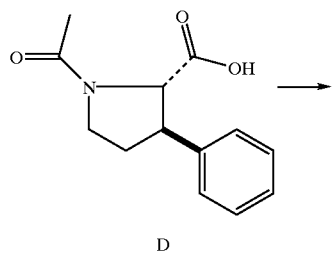

D

-continued

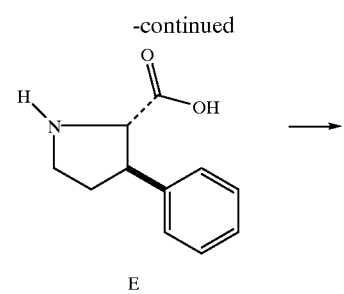

E

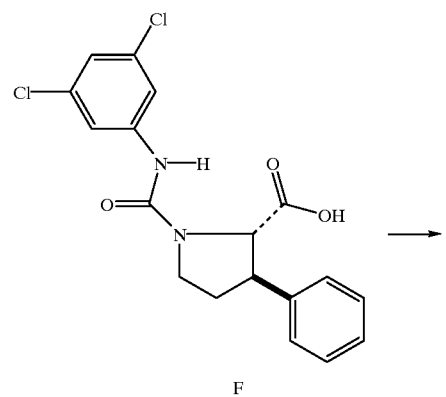

F

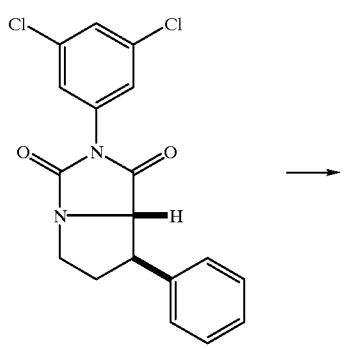

G

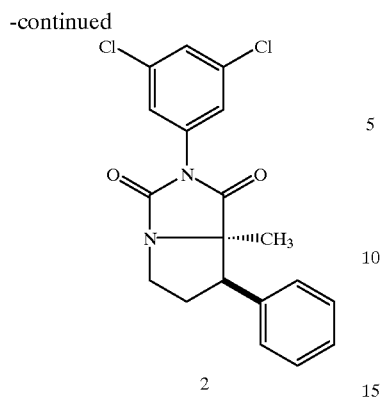

2

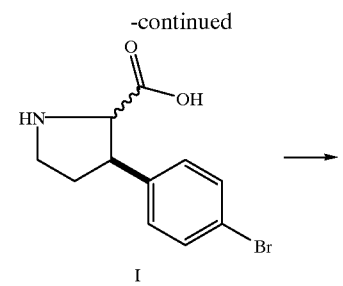

I

Intermediate D (1.0 g, 4.3 mmol), synthesized by the method of Chung et al., *J. Org. Chem.* 1990, 55, 270–275, was heated to reflux in 10 mL of AcOH and 10 mL of concentrated HCl for 6 h. The solvents were removed by rotary evaporation to give 0.98 g of a salt the amino acid E (note: this intermediate is commercially available as a single enantiomer). Intermediate E was then dissolved in 14.3 mL of water containing two equivalents of NaOH and then treated with 3,5-dichlorophenylisocyanate at 50° C. After 2 h the mixture was cooled and treated with concentrated HCl until a precipitate formed. The precipitate was isolated by filtration and dried which provided 280 mg (17%) of intermediate F which was cyclized by heating at 90° C. in 5 mL of 6 N HCl for 3 days. The solid was then extracted into CH$_2$Cl$_2$ and purified by silica gel chromatography (3:1 Hexanes:EtOAc) to yield 220 mg (86%) of intermediate G. Mp 113–114° C.

Intermediate G (90.3 mg, 0.25 mmol) was dissolved in 3 mL of THF and treated with 0.25 mL (0.25 mmol) of a 1 M solution of LDA in hexanes at −78° C. After stirring for 15 min, the mixture was warmed to 0° C. and treated with 0.015 mL (0.25 mmol) of MeI. The solution was allowed to stir at room temperature for 3 h, at which point it was quenched with water, and the organic materials extracted into EtOAc. The EtOAc layers were combined, dried over MgSO$_4$ and concentrated and the desired product was purified by silica gel chromatography using 4:1 Hexanes: EtOAc as the eluant. This produced 48 mg (53%) of the title compound 2, Mp: 133–5° C.

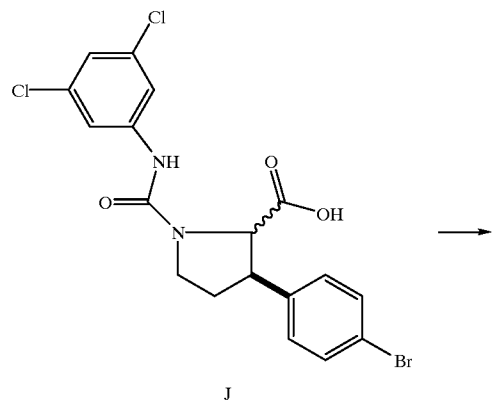

J

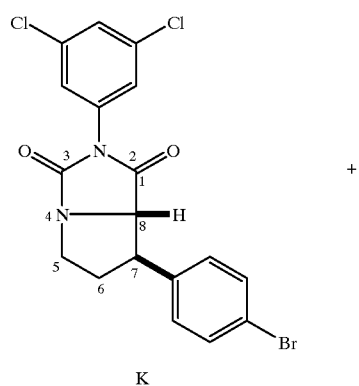

K

Example 3

7-(R*)-(4-Bromophenyl)-2-(3,5-dichorophenyl)-7a-(R*)-tetrahydropyrrolo[1,2-c]imidazole-1,3-dione

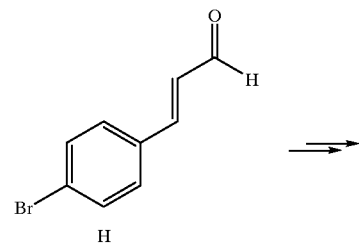

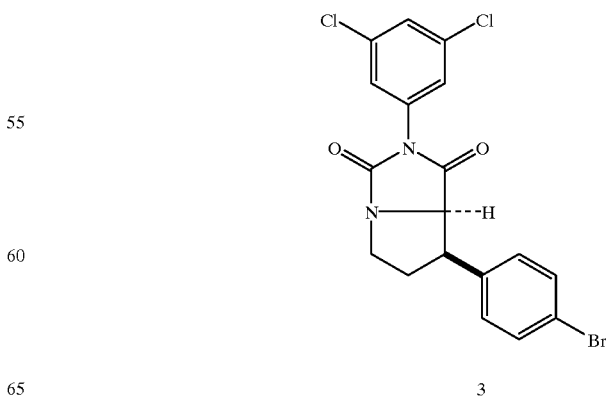

3

Intermediate H was prepared from 4-bromobenzaldehyde via the method reported by Rissanen (*Acta Chem. Scan.* 1989, 43, 787–792) for related compounds. It was converted to intermediate I via the method of Chung et al., *J. Org. Chem.* 1990, 55, 270–275, and then to a diastereomeric mixture of the compounds of Example 3 and K using the technique reported above for the synthesis of the compound of Example 1 (via intermediate J). The two diastereomers were separated by silica gel chromatography (3:1 hexanes:EtOAc giving K, mp: 149–150° C., and the compound of Example 3, mp: 185–6° C.

Examples 4 and 5

2-(3,5-dichlorophenyl)-8a-(R*)-methyl-8-(R*)-phenyl-tetrahydroimidazo[1,5-b]pyridine-1,3-dione and 2-(3,5-dichlorophenyl)-8a-(S*)-methoxy-8-(R*)-phenyl-tetrahydroimidazo[1,5-b]pyridine-1,3-dione, Respectively

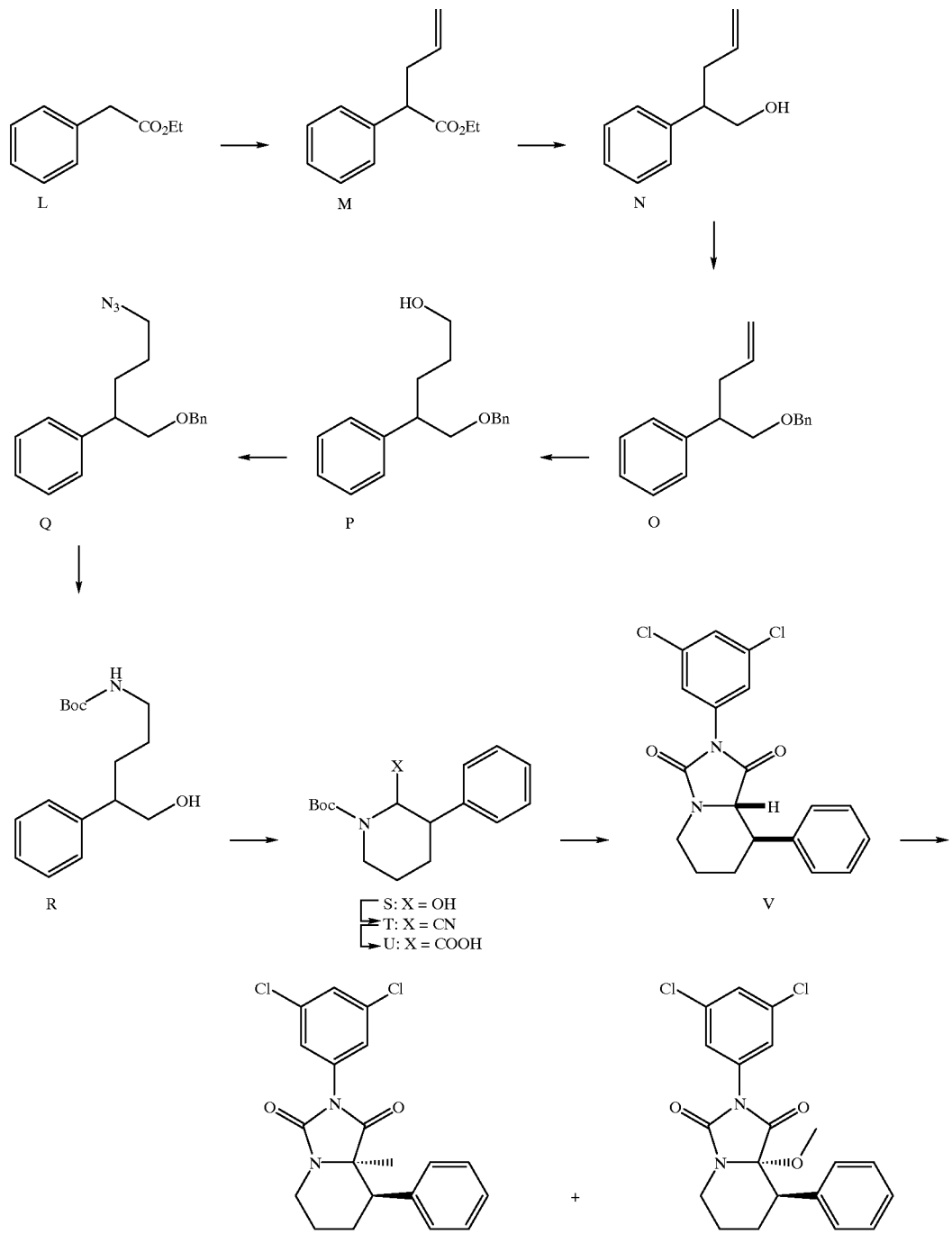

The procedure for the synthesis of intermediate U can be considered a general procedure for the synthesis of 3-arylpipecolic acid derivatives.

To a solution of LDA (70 mmol) in THP (150 mL) was added a solution of ester L (10.0 g, 61 mmol) in THF (50 mL) at −78° C. under a nitrogen atmosphere. The mixture was stirred at −78° C. for 30 min before alkyl bromide (5.8 mL, 67 mmol) was added. The mixture was stirred at −78° C. for 30 min and then room temperature for 2 h. Saturated $NH_4Cl$ (100 mL) was added (with ice bath cooling) and the mixture was extracted into EtOAc, which was dried with $Na_2SO_4$ and concentrated. The residue was purified by silica gel chromatography to give compound M (12.0 g, 96%).

To a solution of ester M (5.0 g, 24.5 mmol) in THF (100 mL) cooled at −78° C. was added DIBAL (1 M in toluene, 61 mL, 61 mmol) dropwise. The mixture was stirred at −78° C. for 30 min then room temperature for 10 h. The reaction was quenched with saturated potassium-sodium tartrate solution at 0° C. The mixture was extracted with EtOAc, dried ($Na_2SO_4$) and concentrated. The residue was purified by silica gel chromatography to give alcohol N (3.17 g, 80%).

A solution of the alcohol N (3.17 g, 20 mmol) in DMF (10 mL) was added to a suspension of NaH (0.94 g, 60%, 24 mmol) in DMF (50 mL) at 0° C. under argon. The mixture was stirred at 0° C. for 30 m, then at room temperature for 1 h and then re-cooled to 0° C. Benzyl bromide (2.6 mL, 21 mmol) was added followed by $Bu_4NI$ (150 mg, 0.4 mmol). The mixture was stirred at 0° C. for 30 min and then at room temperature for 6 h. The reaction was quenched at 0° C. with 1 N HCl (100 mL). The mixture was extracted with EtOAc and washed with a solution of saturated NaCl. Silica gel chromatography gave the benzyl ether O (4.3 g, 87%).

To a solution of intermediate O (4.28 g, 17 mmol) and Wilkinson's catalyst (320 mg, 0.35 mmol) in THF (100 mL) cooled to 0° C. was added catecholborane (1.0 M in THF, 30 mL, 30 mmol) dropwise under argon. The mixture was stirred at room temperature overnight. More reagents (10 mL of catecholborane, 10 mmol; and 200 mg of Wilkinson's catalyst, 0.21 mmol) were added and the mixture was stirred for additional 5 h. The mixture was cooled to 0° C. NaOH (6 M, 25 mL, 150 mmol) was added followed by $H_2O_2$ (30%, 22 mL, 0.19 mmol). The mixture was stirred overnight during which time it was while allowed to warm to room temperature. The mixture was extracted with ether, and the organic layer washed with saturated NaCl, dried and concentrated. The residue was purified by silica gel chromatography to give alcohol P (3.0 g, 65%).

To a solution of the alcohol P (3.14 g, 11.6 mmol) and $Et_3N$ (1.1 mL, 17.4 mmol) in $CH_2Cl_2$ (100 mL) cooled at 0° C. was added slowly mesyl chloride (1.1 mL, 14.2 mmol) under argon. The mixture was stirred for 30 min at 0° C. before water (100 mL) was added. The mixture was extracted with $CH_2Cl_2$ (2×100 mL). The organic layer was washed with water (200 mL), dried with $Na_2SO_4$ and concentrated. The crude material was dissolved in DMF (50 mL) and to the solution was added $NaN_3$ (4 g, 62 mmol). The mixture was stirred at room temperature overnight and concentrated using high vacuum. The residue was redissolved in EtOAc (250 mL), washed with water (2×100 mL) and concentrated to give the azide Q (3.4 g, 99%).

A mixture of the azide Q (3.4g, 11.5 mmol), $Boc_2O$ (3.1 g, 13.8 mmol), 10% Pd/C (0.5 g), EtOH (5 mL), AcOH (5 mL) and EtOAc (100 mL) was shaken in a Parr shaker under $H_2$ (50 psi) overnight. The mixture was filtered through a plug of silica gel and concentrated to give intermediate R (2.6 g, 91%).

To a solution of oxalyl chloride (0.67 mL, 7.68 mmol) in $CH_2Cl_2$ (30 mL) cooled to −78° C. was added a mixture of DMSO (1.00 mL, 14.0 mmol) and $CH_2Cl_2$ (1 mL) dropwise under argon. After 10 m, a solution of the alcohol R (1.07 g, 3.84 mmol) in $CH_2Cl_2$ (10 mL) was added, and the mixture was stirred at −78° C. for 15 min at which time $Et_3N$ (3.2 mL, 22.96 mmol) was added. The mixture was stirred at −78° C. for 10 min and warmed to room temperature. Water (100 mL) was added and the mixture was extracted with $CH_2Cl_2$. The organic layer was dried $Na_2SO_4$) and concentrated and the residue was purified by silica gel chromatography to produce S as a mixture of two diastereomers (0.86 g, 81%).

To a solution of compound S (1.25 g, 4.51 mmol) in $CH_2Cl_2$ (10 mL) cooled to 0° C. was added TFA (4 mL). The solution was stirred at 0° C. for 10 min then at room temperature overnight. The mixture was concentrated and the residue was re-dissolved in a mixture of $CH_3CN$ (30 mL) and $H_2O$ (10 mL). To this solution was added KCN (1.5 g, 23 mmol). The mixture was heated at 60° C. for 10 h, cooled to room temperature, and made basic with $Na_2CO_3$ (solid). The mixture was extracted with EtOAc, and the organic layer was washed with aqueous NaCl (sat.) and concentrated. The crude product was redissolved in $CH_3CN$ and treated with $Boc_2O$ (2.0 g, 8.9 mmol) and DMAP (150 mg). The mixture was stirred at overnight, concentrated and purified by silica gel chromatography to give 521 mg of compound T (40%).

A suspension of the nitrile T (350 mg, 0.59 mmol) in 6 N HCl (10 mL) was refluxed under argon for 48 h. The mixture was concentrated to give the amino acid U (345 mg).

The crude material U from above was dissolved in $H_2O$ (10 mL). The solution was made basic (pH~8) with 2 N NaOH and heated to 60° C. To this mixture was added dropwise a solution of 3,5-dichlorophenylisocyanate (330 mg, 1.68 mmol) in dioxane (4 mL). The mixture was heated for 1 h at 60° C., cooled to 0° C., acidified to pH~1, and extracted with EtOAc. The organic layer was concentrated and re-suspended in 6 N HCl and heated at 90° C. for an additional 4 h. The mixture was extracted with EtOAc, dried $Na_2SO_4$), concentrated. Purification by silica gel chromatography give V (69 mg, 15%).

To a solution of the compound V (20 mg, 0.053 mmol) in THF (2 mL) cooled to −78° C. under argon was added LiHMDS (0.107 mL, 1 M, 0.107 mmol). The mixture was stirred for 30 min and treated with a mixture of HMPA (0.1 mL) and THF (0.1 mL). To the solution was next added MeI (0.020 mL, 0.320 mmol). The mixture was stirred at −78° C. for 30 min then at room temperature overnight. The reaction was quenched at 0° C. with 10% citric acid. The mixture was extracted with EtOAc, dried and concentrated. The residue was purified by preparative TLC (silica gel) to give compounds 4 (10 mg) and 5 (2 mg).

Table 1 illustrates additional compounds of the invention which were prepared by methods analogous to those described above.

TABLE 1

| Example number | Structure |
|---|---|
| 6 | (structure: 3,5-dichlorophenyl-imidazolidinedione-pyrrolidine with CH₃ and 4-bromophenyl substituents) |
| 7 | (structure: 3,5-dichlorophenyl-imidazolidinedione-pyrrolidine with CH₃ and 4-(pyridin-3-yl)phenyl substituents) |
| 8 | (structure: 3,5-dichlorophenyl-imidazolidinedione-pyrrolidine with H and 4-bromophenyl substituents, with OH group) |
| 9 | (structure: 3,5-dichlorophenyl-imidazolidinedione-pyrrolidine with =CH₂ vinyl and 4-bromophenyl substituents) |

TABLE 1-continued

| Example number | Structure |
|---|---|
| 10 | (structure: 3,5-dichlorophenyl-imidazolidinedione-pyrrolidine with CH₃ and 4-bromophenyl substituents, with HO group) |

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol*. 1992, 148,2654–2660). The LFA-1 is purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature*, 1990, 344, 70–72 and see Arruda, A.; et al., *Antimicrob. Agents Chemother*. 1992, 36, 1186–1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 µg/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1; 100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative calorimetric signal proportional to the amount of LFA-1 bound to sICAM-1. Soluble ICAM-1 (60 $\mu$g/mL) is used as a positive control for inhibition of the LFA-1/ICAM-1 interaction. The lack of the addition of LFA-1 to the binding assay is used as a background control for all samples. A dose-response curve is obtained for all test compounds.

All compounds made in the above examples were tested in this assay and each found to have a $K_d$<10 $\mu$M.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the administration of therapeutic or prophylactic amounts of one or more compounds of the formula I.

In accordance with the method provided by the invention, the novel compounds of formula I may be administered for either a "prophylactic" or "therapeutic" purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex tormers (such as PDTA), antioxiants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerini. Microbial preservatives added may include benzalkonium chloride, thimerosal, chloro-butanol or phenylethyl alcohol.

Additionally, the compounds provided by the invention can be administered by suppository.

FORMULATIONS

Compounds of the formula I can be formulated for therapeutic administration in a number $of ways. Descriptions of several exemplary formulations are given below.

Example A

| Capsules or Tablets | | | |
|---|---|---|---|
| Example A-1 | | Example A-2 | |
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

| Parenteral Solutions | |
|---|---|
| Ingredients | Quantity |
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear.

The solution then filtered into the appropriate vials or ampoules and sterilized by autoclaving.

Example C

| Suspension | |
|---|---|
| Ingredients | Quantity |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

What is claimed is:

1. A compound of the formula I,

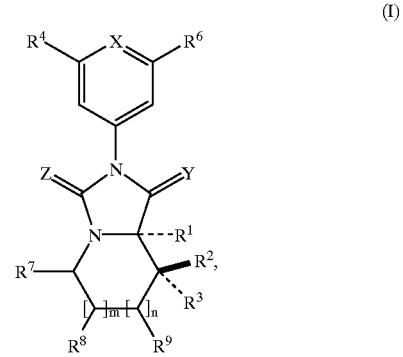

wherein:

m is 0;
n is 1;
Y is an oxygen atom;
Z is an oxygen atom;

$R^1$ is:
  (A) a hydrogen atom, or
  (B) methyl;
$R^2$ is:
  phenyl,
    wherein one or more of the hydrogen atoms of said phenyl group may be optionally and independently replaced with:
      (i) $R^{14}$, which is aryl selected from the class consisting of 3-pyridyl,
      (ii) cyano,
      (iii) nitro, or
      (iv) halogen;
$R^3$ is a hydrogen atom;
$R^4$ is Cl;
X is =CH—;
$R^6$ is Cl;
$R^7$, $R^8$ and $R^9$ are each, independently:
  (A) a hydrogen atom,
  (B) an oxo group, or
  (C) $R^{34}$ or $OR^{34}$,
    wherein $R^{34}$ is defined as:
      (i) a hydrogen atom,
      (ii) branched or unbranched alkyl of 1 to 6 carbon atoms or cycloalkyl of 3 to 6 carbon atoms, which alkyl or cycloakyl group may be mono- or polysubstituted with a group of the formula —$OR^{48}$, wherein $R^{48}$ is a hydrogen atom, or an alkyl of 1 to 7 carbon atoms;
with the proviso that $R^1$ and $R^2$ are in the trans configuration;
or a pharmaceutically acceptable salt thereof.

2. A compound of the formula I, in accordance with claim 1, selected from the group consisting of:

2-(3,5-Dichlorophenyl)-7-(R*)-phenyl-7a-(R*)-tetrahydropyrrolo[1,2-c]imidazole-1,3-dione;

2-(3,5-Dichlorophenyl)-7a-(R*)-methyl-7-(R*)-phenyl-tetrahydropyrrolo[1,2-c]imidazole-1,3-dione;

7-(R*)-4-Bromophenyl)-2-(3,5-dichlorophenyl)-7a-(R*)-tetrahydropyrrolo[1,2-c]imidazole-1,3-dione;

2-(3,5-dichlorophenyl)-8a-(R*)methyl-8-(R*)-phenyl-tetrahydroimidazo[1,5-b]pyridine-1,3-dione;

2-(3,5-dichlorophenyl)-8a-(S*)-methoxy-8-(R*)-phenyl-tetrahydroimidazo[1,5-b]pyridine-1,3-dione;

7-(R*)-(4-Bromophenyl)-2-(3,5-dichlorophenyl)-7a-(R*)-methyl-tetrahydropyrrolo[1,2-c]imidazole-1,3-dione;

2-(3,5-dichlorophenyl)-7-(R*)-[4-(3-pyridyl)phenyl]-7a-(R*)methyl-tetrahydropyrrolo[1,2-c]imidazole-1,3-dione;

7-(R*)-(4-Bromophenyl)-2-(3,5-dichlorphenyl)-6-(S*)-hydroxy-7a-(R*)-tetrahydropyrrolo[1,2-c]imidazole-1,3-dione, 7-(R*)-(4-Bromophenyl)-2-(3,5-dichlorophenyl)-7a-(R*)-allyl-tetrahydropyrrolo[1,2-c]imidazole-1,3-dione; and, 7-(R*)-(4-Bromophenyl)-2-(3,5-dichlorophenyl)-5-(S*)-hydroxy-7a-(R*)-methyl-tetrahydropyrrolo[1,2-c]imidazole-1,3-dione;

or a pharmaceutically acceptable salt thereof.

3. A pharmaceutical composition comprising a compound of the formula I, in accordance with claim 1 or 2.

4. A method for the treatment of an inflammatory disease which comprises administering to a host in need or such treatment an anti-inflammatory amount of a compound of the formula I in accordance with claim 1 or 2.

* * * * *